US009849309B2

(12) United States Patent
Bouzeloc et al.

(10) Patent No.: US 9,849,309 B2
(45) Date of Patent: Dec. 26, 2017

(54) AMINOFUNCTIONAL ORGANOSILOXANES

(71) Applicant: Dow Corning Corporation, Midland, MI (US)

(72) Inventors: Sylvie Bouzeloc, Montigny-le-Tilleul (BE); Severine Cauvin, Mons (BE); Cindy Delvalle, Uccle (BE); Tatiana Dimitrova, Braine-L'Alleud (BE); Sophie Hanssens, Chastre (BE); Lok Ming Eva Li, Midland, MI (US); Elodie Raynaud, Mons (BE); Houria Seghir, Nivelles (BE); Avril E. Surgenor, Waterloo (BE); Blondine Donatienne Van Roy, Wezembeek-Oppem (BE)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/349,674

(22) PCT Filed: Nov. 29, 2012

(86) PCT No.: PCT/US2012/066958
§ 371 (c)(1),
(2) Date: Apr. 4, 2014

(87) PCT Pub. No.: WO2013/082224
PCT Pub. Date: Jun. 6, 2013

(65) Prior Publication Data
US 2014/0234247 A1    Aug. 21, 2014

Related U.S. Application Data

(60) Provisional application No. 61/564,426, filed on Nov. 29, 2011.

(51) Int. Cl.
| *A61K 8/58* | (2006.01) |
| *A61Q 5/02* | (2006.01) |
| *A61Q 5/12* | (2006.01) |
| *A61Q 5/00* | (2006.01) |
| *A61K 8/898* | (2006.01) |
| *C08G 77/26* | (2006.01) |
| *C08L 83/08* | (2006.01) |
| *C08J 3/05* | (2006.01) |
| *A61K 8/39* | (2006.01) |
| *A61K 8/41* | (2006.01) |
| *A61K 8/86* | (2006.01) |

(52) U.S. Cl.
CPC .................. *A61Q 5/00* (2013.01); *A61K 8/39* (2013.01); *A61K 8/416* (2013.01); *A61K 8/585* (2013.01); *A61K 8/86* (2013.01); *A61K 8/898* (2013.01); *A61Q 5/02* (2013.01); *A61Q 5/12* (2013.01); *C08G 77/26* (2013.01); *C08J 3/05* (2013.01); *C08L 83/08* (2013.01); *C08J 2383/08* (2013.01)

(58) Field of Classification Search
CPC .......... A61K 8/416; A61K 8/585; A61Q 5/00; A61Q 5/02; A61Q 5/12; C08J 2383/08; C08J 3/05; C08L 83/08
See application file for complete search history.

(56) References Cited

U.S. PATENT DOCUMENTS

| 2,798,053 A | 7/1957 | Brown |
| 3,958,581 A | 5/1976 | Abegg et al. |
| 3,962,418 A | 6/1976 | Birkofer |
| 4,009,256 A | 2/1977 | Nowak, Jr. et al. |
| 4,559,227 A | 12/1985 | Chandra et al. |
| 4,567,038 A | 1/1986 | Ciaudelli et al. |
| 4,620,878 A | 11/1986 | Gee |
| 4,704,272 A | 11/1987 | Oh et al. |
| 4,710,314 A | 12/1987 | Madrange et al. |
| 4,741,855 A | 5/1988 | Grote et al. |
| 4,820,308 A | 4/1989 | Madrange et al. |

(Continued)

FOREIGN PATENT DOCUMENTS

| CN | 1798792 A | 7/2006 |
| CN | 1823115 A | 8/2006 |

(Continued)

OTHER PUBLICATIONS

Anonymous: "Rinse-Off Conditioner: Color Protection / Formulation 01044", May 28, 2008 (May 28, 2008), pp. 1-2, XP055059516, Retrieved from the Internet: URI:http://www.dowcorning.com/content/publishedlit/FORMUI_01044.pdf [retrieved on Apr. 15, 2003] p. 1, formulation 01044.
Ling, Xu; Polymer Chemistry, 2nd rev., China Petrochemical Press, Jan. 2010, pp. 31-36.
International Search Report for PCT/US2012/066958, dated Apr. 23, 2013, 4 pages.
International Search Report for PCT/US2012/066791, dated Apr. 23, 2013, 4 pages.

(Continued)

*Primary Examiner* — Anna Falkowitz
(74) *Attorney, Agent, or Firm* — Warner Norcross & Judd LLP

(57) ABSTRACT

Aminofunctional silicone compositions are disclosed comprising: an organopolysiloxane having an average formula of $(CH_3)_3SiO[(CH_3)_2SiO]_x[(CH_3)R^NSiO]_ySi(CH_3)_3$ with less than 1 weight % of nitrogen in its formula, where $R^N$ is an aminofunctional group, x is ≥100, y is ≥1 with the proviso the sum of x+y is from 250 to 350; wherein the viscosity of the silicone composition ranges from 1000 to 2500 cP at 25° C. and is measured by a Brookfield RV DV viscometer equipped with Pro CP 52 spindle at 20 RPM; and the aminofunctional silicone composition contains less than 0.1 weight % of D4 and less than 0.1 weight % D5 cyclic siloxanes.

20 Claims, No Drawings

(56) References Cited

U.S. PATENT DOCUMENTS

| | | |
|---|---|---|
| 5,326,483 A | 7/1994 | Halloran et al. |
| 5,543,074 A | 8/1996 | Hague et al. |
| 5,856,544 A | 1/1999 | Czech et al. |
| 5,939,574 A | 8/1999 | Schilling, Jr. et al. |
| 6,153,569 A * | 11/2000 | Halloran ............ 510/119 |
| 6,248,855 B1 | 6/2001 | Dalle et al. |
| 7,501,473 B2 | 3/2009 | Gordon et al. |
| 8,546,483 B2 | 10/2013 | Tanaka et al. |
| 8,815,755 B2 | 8/2014 | Steffanut |
| 2003/0115685 A1 | 6/2003 | Devin-Baudoin et al. |
| 2003/0121108 A1 | 7/2003 | Devin-Baudoin et al. |
| 2003/0126692 A1 | 7/2003 | Devin-Baudoin et al. |
| 2003/0147840 A1 | 8/2003 | Legrand et al. |
| 2003/0152534 A1 | 8/2003 | Legrand et al. |
| 2003/0152541 A1 | 8/2003 | Legrand et al. |
| 2004/0045098 A1 | 3/2004 | Lazzeri |
| 2004/0138373 A1 | 7/2004 | Hamachi et al. |
| 2004/0210074 A1 | 10/2004 | Hupfield et al. |
| 2006/0111452 A1 | 5/2006 | Wallace et al. |
| 2007/0207942 A1 | 9/2007 | Creutz et al. |
| 2008/0282482 A1 | 11/2008 | Audousset et al. |
| 2008/0318825 A1 | 12/2008 | Baumeister |
| 2011/0052521 A1 | 3/2011 | Tanaka et al. |
| 2011/0104085 A1 * | 5/2011 | Klug ............ A61K 8/898 424/59 |
| 2011/0189248 A1 | 8/2011 | Baldaro et al. |
| 2012/0066958 A1 | 3/2012 | McGinnis, Jr. et al. |
| 2013/0040875 A1 | 2/2013 | Henning et al. |
| 2013/0121949 A1 | 5/2013 | Bekemeier et al. |
| 2014/0294746 A1 | 10/2014 | Billes et al. |
| 2014/0308229 A1 | 10/2014 | Bouzeloc et al. |

FOREIGN PATENT DOCUMENTS

| | | |
|---|---|---|
| CN | 101065102 A | 10/2007 |
| CN | 101952350 A | 1/2011 |
| CN | 102006854 A | 4/2011 |
| CN | 102065835 A | 5/2011 |
| CN | 102952272 A | 3/2013 |
| DE | 19707970 | 9/1998 |
| EP | 1312337 A2 | 5/2003 |
| EP | 1312341 A2 | 5/2003 |
| EP | 1312342 A2 | 5/2003 |
| EP | 1312343 A2 | 5/2003 |
| EP | 1312348 A1 | 5/2003 |
| EP | 1312349 A2 | 5/2003 |
| EP | 1312650 A2 | 5/2003 |
| EP | 1543820 A1 | 6/2005 |
| EP | 2186543 A1 | 5/2010 |
| EP | 2557107 A1 | 2/2013 |
| JP | S61097210 A | 5/1986 |
| JP | S61218511 A | 9/1986 |
| JP | H05186601 A | 7/1993 |
| JP | H10095850 A | 4/1998 |
| JP | H11029791 A | 2/1999 |
| JP | 2002255751 | 9/2002 |
| JP | 2003012930 A | 1/2003 |
| JP | 2003155667 A | 5/2003 |
| JP | 2005232141 | 9/2005 |
| JP | 2006291122 A | 10/2006 |
| JP | 2007297533 A | 11/2007 |
| JP | WO2009/116689 * | 9/2009 ............ A61K 8/898 |
| WO | WO9817759 A1 | 4/1998 |
| WO | WO2007071684 A2 | 6/2007 |
| WO | 2011042409 | 4/2011 |
| WO | 2012012524 | 1/2012 |
| WO | 2012027073 | 3/2012 |
| WO | 2013082096 | 6/2013 |
| WO | 2013082112 | 6/2013 |

OTHER PUBLICATIONS

International Search Report for PCT/US2012/066772, dated Aug. 4, 2013, 3 pages.
Machine Assisted Translation of JP2003155667(A), obtained from https://worldwide.espacenet.com/ on Aug. 10, 2016, 23 pages.
Machine Assisted Translation of JP2006291122(A), obtained from https://worldwide.espacenet.com/ on Aug. 10, 2016, 19 pages.
Machine Assisted Translation of JP2007297533(A), obtained from https://worldwide.espacenet.com/ on Aug. 10, 2016, 24 pages.
Machine Assisted Translation of JPH1129791(A), obtained from https://worldwide.espacenet.com/ on Aug. 10, 2016, 15 pages.

* cited by examiner

AMINOFUNCTIONAL ORGANOSILOXANES

CROSS-REFERENCE TO RELATED APPLICATIONS

This application is the National Stage of International Patent Application No. PCT/US2012/66958 filed on Nov. 29, 2012, which claims the benefit of U.S. Provisional Patent Application No. 61/564,426 as filed on Nov. 29, 2011, the contents of which are incorporated herein by reference.

BACKGROUND

Aminofunctional silicones are widely used in hair care products to provide various aesthetic benefits. Formulators of hair care products are continuously seeking improvements in consumer perceivable benefits of such products. As such, there is an ongoing need to identify new aminofunctional silicones that can provide consumer perceived conditioning benefits in a variety of hair care formulations. Any improved aminofunctional silicone composition should also be easily incorporated into hair care products while not affecting the storage stability of the product. In particular, certain silicones may reduce the viscosity of hair care products upon storage. Thus, there is a further need to identify aminofunctional silicone compositions that provide consumer perceivable conditioning benefits in formulated hair care products that are storage stabile.

Reducing the presence of solvents, un-reacted siloxanes, catalyst residues, cyclic polymerization byproducts, and other impurities in aminofunctional silicones is another ongoing challenge in the art. The need to reduce such impurities may arise, among other reasons, when such impurities are incompatible with downstream applications (for example, medical, cosmetic, and personal care applications), where the presence of such impurities would reduce the stability of the product, or where regulatory requirements require removal or reduction of their presence. In particular, there is an interest to reduce the presence of cyclosiloxanes, such as octamethylcyclotetrasiloxanes (D4) and decamethylcyclopentasiloxanes (D5), in aminofunctional silicones compositions. In many instances D4 and D5 may be present in the process to prepare the aminofunctional silicones, alternatively they may be produced from side reactions upon storing the aminofunctional silicone composition.

BRIEF SUMMARY

The present inventors have discovered certain aminofunctional silicone compositions that provide consumer perceivable conditioning benefits in formulated hair care products that are storage stable. Furthermore, the present aminofunctional silicone compositions have reduced D4 and D5 cyclosiloxane contents.

The present aminofunctional silicone compositions comprise:
an organopolysiloxane having an average formula of

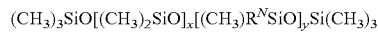

with less than 1 weight % of nitrogen in its formula,
where $R^N$ is an aminofunctional group,
x is ≥100, y is ≥1 with the proviso the sum of x+y is from 250 to 350;
wherein the viscosity of the silicone composition ranges from 1000 to 2500 cP at 25° C. as measured by a Brookfield RV DV viscometer equipped with Pro CP 52 spindle at 20 RPM;
and the aminofunctional silicone composition contains less than 0.1 weight % of D4 and less than 0.1 weight % D5 cyclic siloxanes.

The present disclosure further provides emulsion compositions containing the aminofunctional silicone compositions.

The present disclosure further relates to personal care products containing the aminofunctional silicone compositions or emulsions thereof.

DETAILED DESCRIPTION

The present disclosure relates to aminofunctional silicone compositions comprising, or alternatively consisting essentially of:
an organopolysiloxane having an average formula of

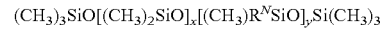

with less than 1 weight % of nitrogen in its formula,
where $R^N$ is an aminofunctional group,
x is ≥100, y is ≥1 with the proviso the sum of x+y is from 250 to 350;
wherein the viscosity of the silicone composition ranges from 1000 to 2500 cP at 25° C. and is preferentially measured by means of a Brookfield RV DV viscometer equipped with Pro CP 52 spindle at 20 RPM;
and the aminofunctional silicone composition contains less than 0.1 weight % of D4 and less than 0.1 weight % D5 cyclic siloxanes.

The organopolysiloxane in the present aminofunctional silicone compositions have an average formula of $(CH_3)_3SiO[(CH_3)_2SiO]_x[(CH_3)R^NSiO]_ySi(CH_3)_3$. The x subscript in the above formula denotes the number of $(CH_3)_2SiO$ units present in the organopolysiloxane, and the y subscript denotes the number of $(CH_3)R^NSiO$ units present in the organopolysiloxane. The number of $(CH_3)_2SiO$ units present in the organopolysiloxane is equal to or greater than 100, that is x is ≥100, alternatively, x may vary from 100 to 340, alternatively from 200 to 300. The number of $(CH_3)R^NSiO$ units present in the organopolysiloxane is equal to or greater than 1, that is y is ≥1, alternatively y may vary from 1 to 50, or alternatively from 1 to 20. The sum of x and y represents the "degree of polymerization" of the organopolysiloxane and should be a value ranging from 250 to 350. The values of x and y may be determined using $^{29}Si$ NMR. Furthermore, the values of x and y may vary providing the particular combination of $(CH_3)_2SiO$ units and $(CH_3)R^NSiO$ units in the organopolysiloxane provides the organopolysiloxane with less than 1 weight % of nitrogen in its formula. As used herein, "weight % of nitrogen" refers to the amount of elemental N in the organopolysiloxane, as determined by analytical methods for assessing elemental nitrogen, such as titration and/or NMR.

The number average ($M_n$) and weight average ($M_w$) molecular weight of the organosiloxane may vary in accordance with the selection of the aminofunctional group and overall degree of polymerization. The number average ($M_n$) may vary from 15,000 to 30,000 g/mole, alternatively from 20,000 to 26,000, alternatively from 21,000 to 24,000. The weight average ($M_w$) may vary from 35,000 to 60,000 g/mole, alternatively from 40,000 to 50,000 g/mole, alternatively from 40,000 to 45,000. Both number and weight average molecular weight may be determined using gel permeation chromatography (GPC) techniques using polystyrene standards for calibration.

The aminofunctional group is designated in the formulas herein as $R^N$ and is illustrated by groups having the formula; —$R^5NHR^6$, —$R^5NR_2^6$, or —$R^5NHR^5NHR^6$, wherein each $R^5$ is independently a divalent hydrocarbon group having at least 1 carbon atom, and $R^6$ is hydrogen or an alkyl group. Each $R^5$ is typically an alkylene group having from 2 to 20 carbon atoms. $R^5$ is illustrated by groups such as; —$CH_2CH_2$—, —$CH_2CH_2CH_2$—, —$CH_2CHCH_3$—, —$CH_2CH_2CH_2CH_2$—, —$CH_2CH(CH_3)CH_2$—, —$CH_2CH_2CH_2CH_2CH_2$—, —$CH_2CH_2CH_2CH_2CH_2CH_2$—, —$CH_2CH_2CH(CH_2CH_3)CH_2CH_2CH_2$—, —$CH_2CH_2CH_2CH_2CH_2CH_2CH_2CH_2$—, and —$CH_2CH_2CH_2CH_2CH_2CH_2CH_2CH_2CH_2CH_2$—. In one embodiment $R^6$ is methyl.

Some examples of suitable amino-functional groups are; —$CH_2CH_2NH_2$, —$CH_2CH_2CH_2NH_2$, —$CH_2CHCH_3NH$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2NHCH_3$, —$CH_2CH_2CH_2NHCH_3$, —$CH_2(CH_3)CHCH_2NHCH_3$, —$CH_2CH_2CH_2CH_2NHCH_3$, —$CH_2CH_2NHCH_2CH_2NH_2$, —$CH_2CH_2CH_2NHCH_2CH_2NH_2$, —$CH_2CH_2CH_2CH_2NHCH_2CH_2NH_2$, —$CH_2CH_2CH_2CH_2NHCH_2CH_2CH_2NH_2$, —$CH_2CH_2NHCH_2CH_2NHCH_3$, —$CH_2CH_2CH_2NHCH_2CH_2CH_2NHCH_3$, —$CH_2CH_2CH_2CH_2NHCH_2CH_2CH_2CH_2NHCH_3$, and —$CH_2CH_2NHCH_2CH_2NHCH_2CH_2CH_3$. In one embodiment, the amino functional group is —$CH_2CH_2CH_2NHCH_2CH_2NH_2$.

The present aminofunctional silicone compositions contain less than 0.1 weight % of D4 and D5 cyclic siloxanes. That is less than 0.1% wt for D4 and independently less than 0.1% wt D5. Alternatively, % of D4 is less than 0.05% or alternatively less than 0.01%. D5 is less than 0.1% or alternatively less than 0.05% or alternatively less than 0.01%.

The weight % of the D4 and D5 cyclics in the silicone composition may be readily determined by any analytical techniques, such as gas chromatography (GC) techniques.

The present disclosure further provides a process for preparing the aminofunctional silicone compositions by reacting:

a) a polydimethylsiloxane having the formula'

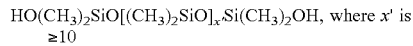

b) a trimethysilyl endblocking compound, and c) an aminofunctional alkoxysilane having the formula $(R^7O)_2(CH_3)SiR^N$.

The reaction in the above process is a condensation polymerization reaction. The reaction may be effected by employing conditions known in the art for effecting condensation reactions. Typically, such conditions affect hydrolysis of components b) and c), such that the hydrolyzed components further condense with each other??? and component a). The reaction effected in the present process may occur simultaneously, that is, where all three component are mixed and reacted. Alternatively, the reaction may proceed in a stepwise manner as further described below.

Component a) in the above process is a polydimethylsiloxane having the formula:

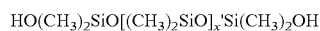

wherein the subscript x' represents the degree of polymerization (DP) of the polydimethylsiloxane. The value for x' is equal to or greater than 10, or may vary from 10 to 500, or alternatively from 10 to 200, or alternatively from 20 to 100, or alternatively from 30 to 60. Polydimethylsiloxanes of the above formula are known in the art and many are commercially available.

Component b) in the above process is a trimethysilyl endblocking compound. Component b) may be selected from those known in the art to act as endblocking groups for organopolysiloxanes. These include, but not limited to; trimethylalkoxysilanes such as trimethylmethoxysilane and trimethylethoxysilane; and hexamethyldisilazane.

Component c) in the above process is an aminofunctional alkoxysilane having the formula $(R^7O)_2(CH_3)SiR^N$, wherein $R^7$ is an alkyl group containing 1 to 4 carbons, and $R^N$ is an aminofunctional group, as defined above. Representative, non-limiting examples include;

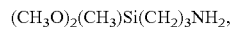
$(CH_3O)_2(CH_3)Si(CH_2)_3NH_2$,

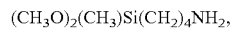
$(CH_3O)_2(CH_3)Si(CH_2)_4NH_2$,

$(CH_3O)_2(CH_3)Si(CH_2)_3NH(CH_2)_2NH_2$,

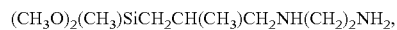
$(CH_3O)_2(CH_3)SiCH_2CH(CH_3)CH_2NH(CH_2)_2NH_2$,

$(CH_3O)_2(CH_3)SiCH_2CH(CH_3)CH_2NH(CH_2)_3NH_2$,

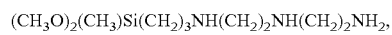
$(CH_3O)_2(CH_3)Si(CH_2)_3NH(CH_2)_2NH(CH_2)_2NH_2$, $(CH_3O)_2(CH_3)Si(CH_2)_3NH(CH_2)_4NH_2$, and similar ethoxy $(C_2H_5O)$ silanes. The amino functional alkoxy silane c) may also be a mixture of two or more independent amino functional alkoxy silanes as described above.

In one embodiment of the present process, the amino functional alkoxy silane is

$(CH_3O)_2(CH_3)Si(CH_2)_3NH(CH_2)_2NH_2$

The above reaction among components a), b), and c) may be carried out at any temperature in the range from 0 to 200° C. Temperatures of at least 50° C. are preferred, most preferably from 60° C. up to 120° C. The reaction may be carried out at pressures in the range from 5 mbar up to 5 bar, for example at ambient pressure; it is frequently preferred that at least the later part of the reaction is carried out under reduced pressure, for example 10 to 400 mbar, particularly if there is a need to promote removal of volatile by-products from the reaction system.

The viscosity of the oranopolysiloxane is preferentially measured at 25° C.; by means of a Brookfield RV DV viscometer equipped with Pro CP 52 spindle at 20 RPM. The same shear rate can be attained by commercial rheometers as, for example, but not restricted to Anton Paar MCR 301, AR1500 from TA instruments. For practical reasons the viscosity is frequently expressed in cSt, that is the ratio between the absolute viscosity measured by means of any of the above-mentioned instruments, expressed in Pa·s or alternatively in Poise) divided by the density of the material measured at the same temperature. It is known in the art that the density of silicones at room temperature is in the range 0.96-1 g/cm3. This means that the numerical values for the absolute and kinematic viscosity (expressed in cP and cSt respectively) are very close, although the units are not equivalent.

The present disclosure further relates to aqueous silicone emulsions comprising:

A) the aminofunctional silicone composition, as described above,

B) a quaternary ammonium surfactant having a formula $R^1R^2R^3R^4N^+X^-$, where $R^1$ is a radical containing at least 10 carbon atoms,
$R^2$ is $R^1$ or a hydrocarbyl containing 1 to 12 carbon atoms,
$R^3$ is $R^1$, $R^2$, or an alcohol group containing 2 to 10 carbon atoms,
$R^4$ is $R^1$, $R^2$, or $R^3$,
$X^-$ is a halide, sulfate, sulfonate, methosulfate, or ethosulfate, and
C) a nonionic surfactant.

In one embodiment, the aqueous silicone emulsion contains less than 0.1 weight % of D4 and D5 cyclic siloxanes, and upon ageing the emulsion for one month at 50° C. the content of D4, D5 or both is lower than one of the following:

0.1 wt. % for D4 or 0.1 wt. % for D5 for the emulsion,
below 0.14 for D4 or 0.07 for D5, when the content is expressed as ratio of the cyclic to the non-water content of the cationic surfactant,
below 1.3 for D4 when the content of the later is expressed as
$((D4_{AGED}-D4_{(t=0)})/\%\ CS)*100$, where D4 is wt % the percentage of D4 in the aged and starting emulsion respectively and % CS is the mass fraction of the cationic surfactant (non-water content) in the emulsion.

The aminofunctional silicone composition used as component a) are those as described above, or may also be a combination of any of the aforementioned aminofunctional silicone compositions used in combination with other organopolysiloxanes. The aminofunctional organopolysiloxane may also be dissolved in a suitable solvent, such as a lower molecular weight organopolysiloxane or organic solvent. The aminofunctional organopolysiloxane used as component a) may also be a blend or a mixture of one or several of the aforementioned aminofunctional organopolysiloxanes with a OH-terminated or trimethyl- or tri-methyl/methoxy PDMS of viscosity of at least 350 cSt at 25° C.

Component B) in the present silicone emulsions is a quaternary ammonium surfactant having a formula R1 R2 R3 R4 N+ X−, where $R^1$ is a radical containing at least 10 carbon atoms,
$R^2$ is $R^1$ or a hydrocarbyl containing 1 to 12 carbon atoms,
$R^3$ is $R^1$, $R^2$, or an alcohol group containing 2 to 10 carbon atoms,
$R^4$ is $R^1$, $R^2$, or $R^3$,
$X^-$ is a halide, sulfate, sulfonate, methosulfate, or ethosulfate.

Alternatively the cationic surfactant may be a mixture of two or more quaternary ammonium species satisfying the description above.

The present emulsions further contain a nonionic surfactant as component C). The nonionic surfactant may be selected from polyoxyethylene based compounds, such as those considered as ethoxylated alcohols. Representative examples of suitable commercially available nonionic surfactants include polyoxyethylene fatty alcohols sold under the tradename BRIJ® by Croda (ICI Surfactants), Wilmington, Del. Some examples are Brij® L23, an ethoxylated alcohol known as polyoxyethylene (23) lauryl ether, and Brij® L4, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S-40. Lutensol® supplied by BASF in the series of Lutensol XP known as ethoxylated, C10-Guerbet alcohol and Lutensol TO known as ethoxylated, iso-C13 alcohol may also be used.

Surfactants whose hydrophilic moiety is based on saccaride or polysaccaride can also be employed. Examples of these are Lutensol® GD70 (BASF) and Triton BG-10 from The Dow Chemical Company (Midland, Mich.).

When mixtures containing nonionic surfactants are used, one nonionic surfactant may have a low Hydrophile-Lipophile Balance (HLB) and the other nonionic surfactant may have a high HLB, such that the two nonionic surfactants have a combined HLB of 11-15, alternatively a combined HLB of 12.5-14.5.

The amount of components A), B), C), and water in the emulsion may vary.

Typically, the emulsions will contain;
15 to 80 wt. % of A) aminofunctional polyorganosiloxane,
    alternatively 30 to 75% A) aminofunctional polyorganosiloxane,
    or alternatively 47 to 71% A) aminofunctional polyorganosiloxane,
0.5 to 10 wt. % of B) quaternary ammonium surfactant,
    alternatively 1.2 to 8 wt. % of B) quaternary ammonium surfactant,
    or alternatively 1.3 to 6.7 wt. % of B) quaternary ammonium surfactant,
2 to 8 wt. % of C) nonionic surfactant,
    alternatively 3 to 7 wt. % of B) nonionic surfactant,
    or alternatively 3.5 to 5.2 wt. % of B) nonionic surfactant,
and sufficient amounts of water, or other components, to sum to 100 wt %.

Other additives can also be incorporated in the emulsions of the present disclosure, such as fillers, viscosity modifiers, foam control agents; anti-freeze agents and biocides.

The present emulsions may be prepared by any known methods, or alternatively prepared by the methods as discussed below.

The present disclosure further provides a process for preparing an emulsion by;
I) forming a mixture comprising;
    A) 100 parts by weight of an aminofunctional organopolysiloxane,
    B) 0.1 to 50 parts by weight of an a quaternary ammonium surfactant,
    C) 0.1 to 50 parts by weight of a non-ionic surfactant,
    (components A, B, and C, are as described above)
II) admixing a sufficient amount of water to the mixture from step I) to form an emulsion,
III) optionally, further shear mixing the emulsion and/or diluting of the emulsion with the continuous phase.

The surfactants B) and C) may be added either alone or in combination with varying amounts of water in step I. Typically, when a surfactant or surfactant combination is selected, the surfactant is added in step I as a concentrated aqueous dispersion, or alternatively as an aqueous solution.

The amount of each surfactant added in step I should be 0.1 to 50 parts by weight for every 100 parts by weight of the aminofunctional organopolysiloxane used. Alternatively, the amount of each surfactant added in step I may be 1 to 50 parts by weight for every 100 parts by weight of the aminofunctional organopolysiloxane used. Alternatively, the amount of surfactants added in step I may be 2 to 20 parts by weight for every 100 parts by weight of the aminofunctional organopolysiloxane used.

Mixing in step (I) can be accomplished by any method known in the art to effect mixing of high viscosity materials. The mixing may occur either as a batch, semi-continuous, or continuous process. Mixing may occur, for example using, batch mixing equipments with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch equipments with high shear actions include Banbury-type (CW Brabender Instruments Inc., NJ) and Henschel type (Henschel mixers America, TX); centrifugal force-based, high shear mixing devices as for example Speed Mixer® (Hauschild & Co KG, Germany). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (N.J.); twin-screw counter-rotating extruders, two-stage extruders, twin-rotor continuous mixers, dynamic or static mixers or combinations of these equipments.

The temperature and pressure at which the mixing of step I occurs is not critical, but generally is conducted at ambient temperature and pressures. Typically, the temperature of the mixture will increase during the mixing process due to the mechanical energy associated when shearing such high viscosity materials.

Step II of the process involves admixing water to the mixture of step I to form an emulsion. Typically 5 to 2000 parts by weight water are mixed for every 100 parts by weight of the step I mixture to form an emulsion. The water is added to the mixture from step I at such a rate, with additional mixing, so as to form an emulsion of the mixture of step I. While this amount of water can vary depending on the selection of the surfactants, generally the amount of water is from 0.1 to 2000 parts per 100 parts by weight of the step I mixture, alternatively from 5 to 500 parts per 100 parts by weight of the step I mixture, or alternatively from 5 to 100 parts per 100 parts by weight of the step I mixture.

The water added to the mixture from step I may be done in incremental portions, whereby each incremental portion comprises less than 30 weight % of the mixture from step I and each incremental portion of water is added successively to the previous after the dispersion of the previous incremental portion of water, wherein sufficient incremental portions of water are added to form an emulsion of the aminofunctional organopolysiloxane.

Mixing in step (II) can be accomplished by any method known in the art to effect mixing of high viscosity materials. The mixing may occur either as a batch, semi-continuous, or continuous process. Any of the mixing methods as described for step (I), may be used to effect mixing in step (II). Alternatively, mixing in step (II) may also occur via those techniques known in the art to provide high shear mixing to effect formation of emulsions. Representative of such high shear mixing techniques include; homogenizers, sonolators, and other similar shear devices.

Optionally, the emulsion formed in step (II) may be further sheared or diluted according to step (III) to reduce particle size and/or improve long term storage stability and/or improve handling. The shearing may occur by any of the mixing techniques discussed above. In some cases it might be necessary to run one or several of the steps I to III under lower pressure or vacuum.

The emulsion products of the present disclosure may be an oil/water emulsion, a water/oil emulsion, a multiple phase or triple emulsion.

In one embodiment, the emulsion products of the present disclosure are oil/water emulsions. The present oil/water emulsions may be characterized by average volume particle of the dispersed organosiloxane block copolymer (oil) phase in the continuous aqueous phase. The particle size may be determined by laser diffraction of the emulsion. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv represents the average volume particle size of the dispersed particles. Dv 0.5 is the particle size measured in volume corresponding to 50% of the cumulative particle population. In other words if Dv 0.5=10 μm, 50% of the particle have an average volume particle size below 10 μm and 50% of the particle have a volume average particle size above 10 μm. Unless indicated otherwise all average volume particle sizes are calculated using Dv 0.5.

The average volume particle size of the dispersed siloxane particles in the oil/water emulsions may vary between 0.1 μm and 150 μm; or between 0.1 μm and 30 μm; or between 0.2 μm and 5.0 μm.

In one embodiment, the present aminofunctional silicone emulsions may be characterized as having less than 0.1 weight % of D4 and D5 cyclic siloxanes. Furthermore, the present aminofunctional silicone emulsions may be characterized as maintaining a low level upon aging of the emulsion. The aging of the present emulsions may be evaluated by storing the emulsion for one month at 50° C. and measuring the D4 and D5 content by gas chromatography (GC) techniques. Upon aging for one month at 50° C. the content D4, D5 or both in the present emulsion is lower than one of the following:

0.1 wt. % for D4 or 0.1 wt. % for D5 for the emulsion,
below 0.14 for D4 or 0.07 for D5, when the content is expressed as ratio of the cyclic to the non-water content of the cationic surfactant,
below 1.3 for D4 when the content of the later is expressed as
$((D4_{AGED}-D4_{(t=0)})/\% \ CS)*100$, where D4 is wt % the percentage of D4 in the aged and starting emulsion respectively and % CS is the mass fraction of the cationic surfactant (non-water content) in the emulsion.

The present emulsions are useful to treat a variety of fiber surfaces. The fiber surfaces include various textile and natural fibers. Fibers or textiles that can be treated with the treatment composition include natural fibers such as cotton, silk, linen, and wool; regenerated fibers such as rayon and acetate; synthetic fibers such as polyesters, polyamides, polyacrylonitriles, polyethylenes, and polypropylenes; combinations, and blends thereof. The form of the fibers can include threads, filaments, tows, yarns, woven fabrics, knitted materials, non-woven materials, paper, carpet, and leather.

The fiber treatment composition comprising the present emulsions can be applied to the fiber and/or textile during making the fibers or textiles, or later via a post application process. After application, carriers (if any) can be removed from the treatment composition for example by drying the composition at ambient or elevated temperature. The amount of treatment composition applied to the fibers and textiles is typically sufficient to provide 0.1 to 15 weight percent of the composition on the fibers and textiles, based on their dry weight, preferably in an amount of 0.2 to 5 weight percent based on the dry weight of the fiber or textile.

The use of the compositions according to the invention on hair may use a conventional manner for conditioning hair. An effective amount of the composition for conditioning hair is applied to the hair. Such effective amounts generally range from about 0.5 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair.

The present aminofunctional silicone compositions, or emulsions thereof, may be formulated into personal care product compositions. The personal care compositions of this invention may be in the form of a cream, a gel, a powder, a paste, or a freely pourable liquid. Generally, such compositions can generally be prepared at room temperature if no solid materials at room temperature are presents in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

In yet another aspect the present emulsions can be used as part of colorant of fixative compositions and applied as pre-, during-, post-treatment in the process of coloring or perming hair. The purposes could range from color retention and color enhancement to again conditioning of the colored hair fibers. Examples and preferred embodiments can be found in the patent documents EP1312343A2, EP1312348A2, EP1312349A2, EP1312337, EP1312650, EP1312342 A2, EP1312341 A2, WO2007071684, US20080282482 by L'Oreal and EP1543820 by Procter and Gamble, all of which are incorporated herein by reference.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from about 1 mg/cm2 to about 3 mg/cm2. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 0.5 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit.

Non-limiting examples of additives which may be formulated into the personal care compositions in addition to the present aminofunctional silicone compositions include: additional silicones, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, fragrances, waxes, rheology-modifying agents, anti-dandruff, anti-acne, anti-carrie and wound healing-promotion agents.

The personal care composition, such as a shampoo or cleanser may contain at least one anionic detersive surfactant. This can be any of the well-known anionic detersive surfactants typically used in shampoo formulations. These anionic detersive surfactants function as cleansing agents and foaming agents in the shampoo compositions of this invention. The anionic detersive surfactants are exemplified by alkali metal sulfonates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including CH3(CH2)6CH2O (C2H4O)2SO3H, CH3(CH2)7CH2O(C2H4O)3.5SO3H, CH3(CH2)8CH2O(C2H4O)8SO3H, CH3(CH2)19CH2O (C2H4O)4SO3H, and CH3(CH2)10CH2O(C2H4O)6SO3H, sodium salts, potassium salts, and amine salts of alkylnaphthylsulfonic acid. Preferably the detersive surfactant is selected from the group consisting of sodium lauryl sulfate, ammonium lauryl sulfate, triethanolamine lauryl sulfate, sodium lauryl ether sulfate, and ammonium lauryl ether sulfate. The anionic detersive surfactant is present in the shampoo compositions of this invention in an amount from about 5 to 50 wt % and preferably about 5 to 25 wt % based on the total weight of the composition.

The personal care composition may contain at least one cationic deposition aid, preferably a cationic deposition polymer. The cationic deposition aid will generally be present at levels of from 0.001 to 5%, preferably from about 0.01 to 1%, more preferably from about 0.02% to about 0.5% by weight. The polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof. The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8. The cationic nitrogen-containing group will generally be present as a substituent on a fraction of the total monomer units of the cationic deposition polymer. Thus when the polymer is not a homopolymer it can contain spacer noncationic monomer units. Such polymers are described in the CTFA Cosmetic Ingredient Directory, 3rd edition. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are preferred. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the C, —C., alkyls, more preferably C, and C2 alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide. The cationic deposition aids can comprise mixtures of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256; and cationic polyacrylamides as described in our copending UK Application No. 9403156.4 (WO95/22311). Other cationic deposition aids that can be used include polysaccharide polymers, such as cationic cellulose derivatives and cationic starch derivatives. Cationic polysaccharide polymer materials suitable for use in compositions of the invention include those of the formula: $A\text{-}O(R\text{—}N^+R^1R^2R^3X^-)$ wherein: A is an anhydroglucose residual group, such as starch or cellulose anhydroglucose residual, R is an alkylene oxyalklene, polyoxyalkylene, or hydroxyalkylene group, or combination thereof, R', R~' and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R', R 2 and R') preferably being about 20 or less, and X is an anionic counterion, as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

The personal care composition may contain a foam boosting agent. A foam booster is an agent which increases the amount of foam available from a system at a constant molar concentration of surfactant, in contrast to a foam stabilizer which delays the collapse of a foam. Foam building is provided by adding to the aqueous media an effective amount of a foam boosting agent. The foam boosting agent is preferably selected from the group consisting of fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Preferably a foam booster is selected from the group consisting of lauric acid diethanolamide, N-lauryl dimethylamine oxide, coconut acid diethanolamide, myristic acid diethanolamide, and oleic acid diethanolamide. The foam boosting agent is preferably present in the shampoo compositions of this invention in an amount from about 1 to 15 wt % and more preferably about 2 to 10 wt % based on the total weight of the composition. The composition may further comprise a polyalkylene glycol to improve lather performance. Concentration of the polyalkylene glycol in the shampoo composition may range from about 0.01% to about 5%, preferably from about 0.05% to about 3%, and more preferably from about 0.1% to about 2%, by weight of the composition. The optional polyalkylene glycols are characterized by the general formula: H(OCH2CHR)n-OH wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from about 1500 to about 25,000, preferably from about 2500 to about 20,000, and more preferably from about 3500 to about 15,000. Polyethylene glycol polymers useful herein are PEG-2M wherein R equals H and n has an average value of about 2,000 (PEG-2M is also known as Polyox WSR9 N-10, which is available from Union Carbide and as PEG-2,000); PEG-5M wherein R equals H and n has an average value of about 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and n has an average value of about 7,000 (PEG-7M is also known as Polyox WSRO N-750 available from Union Carbide); PEG-9M wherein R equals H and n has an average value of about 9,000 (PEG 9-M is also known as Polyox WSRS N-3333 available from Union Carbide); and PEG14 M wherein R equals H and n has an average value of about 14,000 (PEG-14M is also known as Polyox WSRO N-3000 available from Union Carbide). Other useful polymers include the polypropylene glycols and mixed polyethylene/polypropylene glycols.

The personal care composition may contain a suspending agent at concentrations effective for suspending the preferred silicone conditioning agent, or other water-insoluble material, in dispersed form in the shampoo compositions. Such concentrations range from about 0.1% to about 10%, preferably from about 0.3% to about 5.0%, by weight of the shampoo compositions. Suspending agents include crystalline suspending agents which can be categorized as acyl derivatives, long chain amine oxides, and mixtures thereof, concentrations of which range from about 0.1% to about 5.0%, preferably from about 0.5% to about 3.0%, by weight of the shampoo compositions. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having C8-C22 chains may be used. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g., stearyl dimethyl amine oxide. Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference. Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company. Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

EXAMPLES

The following examples are included to demonstrate the invention to those of skill in the art. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Comparative Aminofunctional Organopolysiloxanes

The following are commercially available aminofunctional organopolysiloxanes used as comparative examples. Their physical characteristics listed are taken from the corresponding MSDS and/or technical documentation sheets.

AP-8087 A 5000 cP, Dimethyl, Methyl Aminoethylaminoisobutyl siloxane, methoxy & hydroxyl terminated, commercially available under the name DowCorning® AP-8087 (Dow Corning Corp., Midland, Mich.)

AP-8566 A 3500 cSt Dimethyl, methyl (aminoethylaminoisobutyl) siloxane, nitrogen content of less 1%, 1-5% cyclic siloxanes, commercially available under the name DowCorning® AP-8566. (Dow Corning Corp., Midland, Mich.)

AP-8468 A 5000-15000 cP Dimethyl, (aminoethylaminopropyl) methyl siloxane with nitrogen content of 0.6%, Available as OFX-8468 FLUID from Xiameter (Dow Corning Corp., Midland, Mich.).

Example 1

Preparation of Aminofunctional Silicone Composition AP1

First, 490 g of a OH-terminated polydimethylsiloxane (DOW CORNING® 2-1273 FLUID), 3.75 g of hexamethyldisilazane, and 0.1 g of trifluoroacetic acid were added to a 1 L 3-necked round-bottomed flask fitted with a crescent-shaped paddle stirring rod, a water cooled condenser and a thermometer adaptor itself fitted with a thermal couple, all under nitrogen purge. The reaction mixture was heated to 70° C. at moderate stirring and held for 3 h reflux and then 6.67 g of aminoethylaminopropylmethyldimethoxysilane was added to the reaction followed by the addition of a small amount 0.2 wt. % Octanoic acid. The reaction continued at 80° C. and reflux for 3 h. 24 h later the reaction mixture was stripped for 10 h at 94° C. and under reduced pressure and moderate stirring. The resulting aminofunctional organosiloxane appeared clear and colorless. 29Si NMR was used to characterize the polymer and a DP of 319 is obtained from the ratio between D and M units. The viscosity was 2024 cP as measured by means of a Brookfield RV DV viscometer equipped with Pro CP 52 spindle at 20 RPM at 25 C. The % N was obtained by titration and was 0.16%. Molecular weight was obtained using standard GPC with polystyrene standards, the amount of cyclic silicones was determined by means of Gas Chromatography. Values are provided in Table 1.

Example 2

Preparation of an Aminofunctional Silicone Composition AP2

Essentially the same process was used as in Example 1. First 477 g of the OH-terminated polydimethylsiloxane and 9.9 g of ethoxytrimethylsilane instead of hexamethyldisilazane were used. This process results in a clear colorless polymer with DP of 269 (value obtained by NMR); viscosity of 1769 cP and % N of 0.16%. Further characteristics are provided in Table 1.

TABLE 1

| | FRESH | |
|---|---|---|
| | Ex 1 | Ex 2 |
| Mn g/mol | 21,200 | 22,800 |
| Mw g/mol | 42,700 | 42,100 |
| Mz g/mol | 77,700 | 70,500 |
| ppm D4. | <5 | <5 |
| ppm D5. | <5 | <5 |
| viscosity, cP | 2024 | 1761 |

Example 3

Different amino polymers were formulated in a shampoo and the influence of the polymer on the viscosity of the formulation was observed. An amino polymer of preparation Example 2 and AP-8087 do not decrease the initial viscosity of the formulation. The incorporation of the AP 8566 or AP-8468 decreases the viscosity by a factor of 3 to 4 (Table 2). Moreover, over their usable shelf life, the formulations containing AP2 and AP-8087 have a substantially higher viscosity than the formulations containing AP-8566 or AP-8468 (compare samples A1-Ref to A2-A5 at the same storage time in table 2). However, AP-8087 is methoxy-terminated organopolysiloxane and tends to self-condense upon storage, which is a disadvantage in industrial setting.

TABLE 2

| | Ingredients | A1-REF | A2 | A3 | A4 | A5 |
|---|---|---|---|---|---|---|
| Phase A | Empicol ESB3 | 30.0% | 30.0% | 30.0% | 30.0% | 30.0% |
| | Water | to 100% | to 100% | to 100% | to 100% | to 100% |
| | Glucamate DOE120 | 1.5% | 1.5% | 1.5% | 1.5% | 1.5% |
| | Rewoderm S1333 | 4.0% | 4.0% | 4.0% | 4.0% | 4.0% |
| | Amonyl 380BA | 4.0% | 4.0% | 4.0% | 4.0% | 4.0% |
| Phase B | Comperlan KD | 4.0% | 4.0% | 4.0% | 4.0% | 4.0% |
| Phase C | Polymer of Invention AP2 | | 2% active | | | |

TABLE 2-continued

| | Ingredients | A1-REF | A2 | A3 | A4 | A5 |
|---|---|---|---|---|---|---|
| | AP-8087 | | | 2% active | | |
| | AP-8566 | | | | 2% active | |
| | AP-8468 | | | | | 2% active |
| Phase D | Citric acid (50%) to pH = 5.5 | q.s. | q.s. | q.s. | q.s. | q.s. |
| | Appearance | Clear | Slightly white/grey opaque | Slightly white/grey opaque | Clear | Clear |
| viscosity, spindle 5, 1 rpm | Just after formulation | 151000 | 123000 | 133000 | 34400 | 42000 |
| | 24 h | 137000 | 98000 | 110000 | 32000 | 30200 |
| | 1 week | 193000 | 90400 | 104000 | 40400 | 35800 |
| | 2 weeks | 183000 | 82400 | 96400 | 39800 | 36600 |
| | 3 weeks | 187000 | 81200 | 98400 | 38900 | 36800 |
| | 1 month | 191000 | 72800 | 94800 | 39800 | 35800 |
| | 3 months | 168000 | 62000 | 84000 | 34100 | 30200 |
| | 4 months | 154000 | 59600 | 78800 | 32200 | 28200 |
| | 5 months | 152000 | 52400 | 74000 | 29900 | 26200 |
| | 6 months | 178000 | 56800 | 79600 | 32000 | 28500 |

Example 4

Polymers AP 8087, AP2 and AP-8468 were formulated in a rinse off formulation. Caucasian bleached hair tresses were treated with the rinse-off conditioner formulations and forces required to drive a comb through a tress of hair were measured using a Dia-Stron MTT-175 (Dia-Stron Limited, UK). The test was run in an environmentally controlled room with a constant temperature of 20° C. and fixed relative humidity of 50%. Total combing load was obtained from UvWin software. Statistical analysis was run with the data generated.

Generally the lower the combing force/load the better the performance. Without being bound to any theory, for the consumer the low combing load translates into one or more of the following:

Ease of detangling

Less detangled

Ease of styling

Smooth/soft

Supple

Reduced friction

Easy to manage

The list above is not exhaustive and is meant solely to illustrate the importance of the measurement value for the practice. A person skill in the art will understand that different adjectives along the lines above can be used to describe hair characterized with a low dry or wet combing load. Hair tresses were treated with the rinse-off formulation and the combing load was measured in wet and dry state. It has been found (table 3) that rinse off comprising the polymer of the invention (AP2) provides lower combing load than the comparative examples. Values marked with * are statistically different from the polymer of the invention with $p<0.01$. (Table 3)

TABLE 3

| | Combing Load, J | | | |
|---|---|---|---|---|
| | dry avg | wet avg | dry std dev | wet std dev |
| AP-8468 | 0.094* | 0.881* | 0.012 | 0.215 |
| AP2 - invention | 0.054 | 0.287 | 0.011 | 0.074 |
| AP-8087 | 0.066* | 0.811* | 0.011 | 0.171 |

Example 5

Emulsification

The polymer AP2 of the present invention was emulsified using shear equipment with capacity of 10 L. The AP2, surfactants (cationic and nonionic) and some water were put in the kettle and subjected to vigorous shear to produce emulsion via catastrophic phase inversion. Thus produced concentrated emulsion was then diluted to about 50% silicone. Then the thickener was dispersed followed by the adjustment of the pH to 7.2 by adding small amount of sulfuric acid. Last, a cosmetically acceptable biocide has been added. Table 4 summarizes the composition of EM-AP2 emulsion.

TABLE 4

| Ingredients in EM -AP2 | % |
|---|---|
| AP2 | 49.95 |
| Arquad 16-29 (cationic surfactant) | 6.41 |
| C13E6 (nonionic surfactant) | 4.24 |
| Cellulose based thickener | 0.25 |
| Biocide | 0.9 |
| Water | q.s. 100 |

Shine/Luster Evaluation

EM-AP2 was formulated in hair care rinse-off conditioner. A comparative example is prepared using Dow Corning® 949 cationic emulsion. Caucasian bleached hair tresses were treated with the rinse-off conditioner formulations. Treatment level corresponds to 0.4 g formulated rinse-off/1 g hair. The rinse-off formulations contained 2% Silicone.

The tresses (treated and untreated; 3 independent tresses per formulation, 3 reading points per tress) were evaluated for shine/luster using commercial Samba equipment from Bossa Nova Technologies. The instrument measures specular reflection (shine) and second reflection (chroma) and the diffuse reflection of light from the hair to determine the luster value.

For the consumer the increase in luster value can also be expressed as:
Brilliance
Liveliness/Vitality
Healthy The list above is not exhaustive and is meant solely to illustrate the importance of the measurement value for the practice. A person skill in the art will understand that different adjectives along the lines above can be used to describe hair characterized with increased shine/luster.

Upon treatment, the emulsion according to this invention provides for higher shine than the commercial reference e.g. Dow Corning® 949 cationic emulsion (Table 5)

TABLE 5

| Emulsion Code | % change in luster treated vs. untreated tresses ± STDEV |
|---|---|
| EM-AP2 | −4.4* ± 1.9 |
| DC 949 | −11.4 ± 4.9 |

*Statistically different from the reference with confidentiality of 95%

The invention claimed is:

1. An aqueous emulsion comprising:
A) an aminofunctional silicone composition comprising an organopolysiloxane having an average formula:

$(CH_3)_3SiO[(CH_3)_2SiO]_x[(CH_3)R^NSiO]_ySi(CH_3)_3$ with less than 1 weight % of nitrogen in its formula, where $R^N$ is an aminofunctional group, x is ≥100, and y is ≥1, with the proviso that the sum of x+y is from 250 to 350;
wherein the viscosity of A) the aminofunctional silicone composition ranges from 1000 to 2500 cP at 25° C. as measured by a Brookfield RV DV viscometer equipped with Pro CP 52 spindle at 20 RPM; and
wherein A) the aminofunctional silicone composition contains less than 0.1 weight % of octamethylcyclotetrasiloxanes (D4) and less than 0.1 weight % decamethylcyclopentasiloxanes (D5);
B) a quaternary ammonium surfactant having a formula:

$R^1R^2R^3R^4N^+X^-$, where $R^1$ is a radical containing at least 10 carbon atoms, $R^2$ is $R^1$ or a hydrocarbyl containing 1 to 12 carbon atoms, $R^3$ is $R^1$, $R^2$, or an alcohol group containing 2 to 10 carbon atoms, $R^4$ is $R^1$, $R^2$, or $R^3$, and $X^-$ is a halide, sulfate, sulfonate, methosulfate, or ethosulfate;
wherein B) the quaternary ammonium surfactant is present in the aqueous emulsion in an amount of at least 0.5 wt. %; and
C) a nonionic surfactant.

2. The aqueous emulsion of claim 1, wherein the aminofunctional group $R^N$ has the formula $-CH_2CH_2CH_2NHCH_2CH_2NH_2$.

3. A process for preparing the aqueous emulsion of claim 1 comprising the steps of:
I) reacting
a) a polydimethylsiloxane having the formula:

$HO(CH_3)_2SiO[(CH_3)_2SiO]_{x'}Si(CH_3)_2OH$, where x' is ≥10 b) a trimethysilyl endblocking compound, and
c) an aminofunctional alkoxysilane having the formula:

$(R^7O)_2(CH_3)SiR^N$, wherein $R^7$ is an alkyl group containing 1 to 4 carbons, and
$R^N$ is an aminofunctional group,
to prepare A) the aminofunctional silicone composition; and
II) mixing A) the aminofunctional silicone composition, B) the quaternary ammonium surfactant, C) the nonionic surfactant, and water to prepare the aqueous emulsion.

4. The process of claim 3, wherein b) the trimethysilyl endblocking compound is trimethylethoxysilane.

5. The process of claim 3, wherein a) the polydimethylsiloxane and b) the trimethylsilyl endblocking compound are first reacted to form a partially endblocked polydimethylsiloxane intermediate, and then further reacting the polydimethylsiloxane intermediate with c) the aminofunctional alkoxysilane to form A) the aminofunctional silicone composition.

6. The process of claim 3, wherein b) the trimethysilyl endblocking compound is hexamethyldisilazane.

7. The process of claim 5, wherein a) the polydimethylsiloxane and b) the trimethylsilyl endblocking compound are first reacted in the presence of an acidic catalyst to form a partially endblocked polydimethylsiloxane intermediate.

8. The process of claim 7, wherein the acidic catalyst is trifluoroacetic acid.

9. The process of claim 5, wherein the polydimethylsiloxane intermediate is reacted with c) the aminofunctional alkoxysilane in the presence of an organic acid to form A) the aminofunctional silicone composition.

10. The process of claim 9, wherein the organic acid is octanoic acid.

11. A personal care product comprising the aqueous emulsion of claim 1.

12. The personal care product of claim 11, wherein the personal care product is a hair care product.

13. The personal care product of claim 11, wherein the personal care product is a leave-on conditioner, a rinse-off conditioner, a hairspray, gel, a styling composition, or a hair-dyeing composition.

14. The aqueous emulsion of claim 1, comprising 15 to 80 wt. % of A) the aminofunctional silicone composition.

15. The aqueous emulsion of claim 1, comprising 0.5 to 10 wt. % of B) the quaternary ammonium surfactant.

16. The aqueous emulsion of claim 1, comprising 2 to 8 wt. % of C) the nonionic surfactant.

17. The process of claim 3, further comprising the step(s) of shear-mixing the aqueous emulsion and/or diluting of the aqueous emulsion with the continuous phase.

18. A process for preparing the aqueous emulsion of claim 1 comprising the steps of:
I) forming a mixture comprising;
A) 100 parts by weight of the aminofunctional organopolysiloxane,
B) 0.1 to 50 parts by weight of the quaternary ammonium surfactant, and
C) 0.1 to 50 parts by weight of the nonionic surfactant;
II) admixing water to the mixture from step I) to form the aqueous emulsion; and
III) optionally, further shear mixing the aqueous emulsion and/or diluting of the aqueous emulsion with the continuous phase.

19. The aqueous emulsion of claim 15, comprising 1.2 to 8 wt. % of B) the quaternary ammonium surfactant.

20. The aqueous emulsion of claim 19, comprising 1.3 to 6.7 wt. % of B) the quaternary ammonium surfactant.

\* \* \* \* \*